(12) United States Patent
Vetter et al.

(10) Patent No.: US 10,064,610 B2
(45) Date of Patent: Sep. 4, 2018

(54) DEVICES AND METHODS FOR SOFT TISSUE BIOPSY AND TISSUE SAMPLE COLLECTION

(71) Applicant: TransMed7, LLC, Portola Valley, CA (US)

(72) Inventors: James W Vetter, Portola Valley, CA (US); Eugene H Vetter, Portola Valley, CA (US)

(73) Assignee: TransMed7, LLC, Portola Valley, CA (US)

( * ) Notice: Subject to any disclaimer, the term of this patent is extended or adjusted under 35 U.S.C. 154(b) by 0 days.

(21) Appl. No.: 15/059,784

(22) Filed: Mar. 3, 2016

(65) Prior Publication Data

US 2017/0055966 A1    Mar. 2, 2017

Related U.S. Application Data

(60) Provisional application No. 62/127,722, filed on Mar. 3, 2015.

(51) Int. Cl.
*A61B 10/02* (2006.01)
*A61B 17/28* (2006.01)
(Continued)

(52) U.S. Cl.
CPC ...... *A61B 10/0283* (2013.01); *A61B 10/0096* (2013.01); *A61B 10/0266* (2013.01);
(Continued)

(58) Field of Classification Search
CPC . A61B 10/0283; A61B 10/0096; A61B 17/28; A61B 10/0266;
(Continued)

(56) References Cited

U.S. PATENT DOCUMENTS 4,563,178 A * 1/1986 Santeramo .......... A61M 5/1782
                                                         141/27
5,373,854 A   12/1994 Kolozsi
(Continued)

FOREIGN PATENT DOCUMENTS

WO    2013056190 A1    4/2013

OTHER PUBLICATIONS

EPO Examination Report dated Aug. 11, 2016 in EP Appln 12839250.3.
(Continued)

*Primary Examiner* — David J McCrosky
(74) *Attorney, Agent, or Firm* — Young Law Firm, P.C.

(57) ABSTRACT

A device comprises a syringe comprising a syringe body portion and a plunger portion configured to engage with and slide axially within the body portion; a tube set fitted to the syringe. The tube set may comprise a proximal tube attached to the plunger portion at a proximal end thereof and terminated, at a distal end thereof, by a beak assembly configured to assume a first configuration suitable for coring through tissue and a second configuration suitable for tissue penetration and parting off tissue; and a distal tube disposed over and coupled to the proximal tube to enable travel-limited axial displacement relative to the proximal tube. Axially moving the plunger portion of the plunger portion within the body portion of the syringe causes differential movement of the proximal tube relative to the distal tube to selectively cause the beak assembly to assume the first or the second configuration.

22 Claims, 8 Drawing Sheets

(51) Int. Cl.
    *A61M 1/00*     (2006.01)
    *A61B 10/00*     (2006.01)
    *A61M 25/06*     (2006.01)
    *A61B 17/3205*     (2006.01)
    *A61B 17/00*     (2006.01)
    *A61B 17/32*     (2006.01)

(52) U.S. Cl.
CPC ............ *A61B 17/28* (2013.01); *A61M 1/007* (2014.02); *A61M 25/0662* (2013.01); *A61B 17/32053* (2013.01); *A61B 2010/0208* (2013.01); *A61B 2017/00862* (2013.01); *A61B 2017/320064* (2013.01); *A61B 2217/005* (2013.01)

(58) Field of Classification Search
CPC .. A61B 2017/320064; A61B 2217/005; A61B 2010/0208; A61B 17/32053; A61M 25/0662; A61M 1/007
See application file for complete search history.

(56) References Cited

U.S. PATENT DOCUMENTS

| | | | | |
|---|---|---|---|---|
| 5,706,824 A | * | 1/1998 | Whittier | A61B 10/06 600/564 |
| 6,083,150 A | * | 7/2000 | Aznoian | A61B 10/06 600/564 |
| 6,086,543 A | | 7/2000 | Anderson | |
| 6,110,127 A | * | 8/2000 | Suzuki | A61B 10/06 600/564 |
| 6,322,522 B1 | | 11/2001 | Zimmon | |
| 8,118,755 B2 | | 2/2012 | Hibner | |
| 8,133,237 B2 | | 3/2012 | Oostman, Jr. et al. | |
| 8,568,410 B2 | | 10/2013 | Vakharia | |
| 8,579,897 B2 | | 11/2013 | Vakharia | |
| 8,603,135 B2 | | 12/2013 | Mueller | |
| 8,696,671 B2 | | 4/2014 | Solsberg et al. | |
| 2010/0121153 A1 | | 5/2010 | To | |
| 2012/0209140 A1 | | 8/2012 | Ryan | |
| 2013/0096459 A1 | | 4/2013 | Vetter | |
| 2014/0142602 A1 | | 5/2014 | Polo | |

OTHER PUBLICATIONS

USPTO Notice of Allowance dated Jan. 18, 2017 in U.S. Appl. No. 14/052,724.
USPTO Office Action dated Mar. 17, 2017 in U.S. Appl. No. 13/853,719.
USPTO Office Action dated Apr. 19, 2017 in U.S. Appl. No. 14/599,481.
USPTO Office Action dated Apr. 19, 2017 in U.S. Appl. No. 14/050,771.
USPTO Office Action dated May 22, 2017 in U.S. Appl. No. 14/491,348.
EPO Extended European Search Report dated Jun. 28, 2017 in EPO Appln. 14804925.7.
USPTO Notice of Allowance dated Jul. 5, 2017 in U.S. Appl. No. 13/853,806.
EPO Extended European Search Report dated Jun. 17, 2017 in EPO Appln. 14794839.2.

* cited by examiner

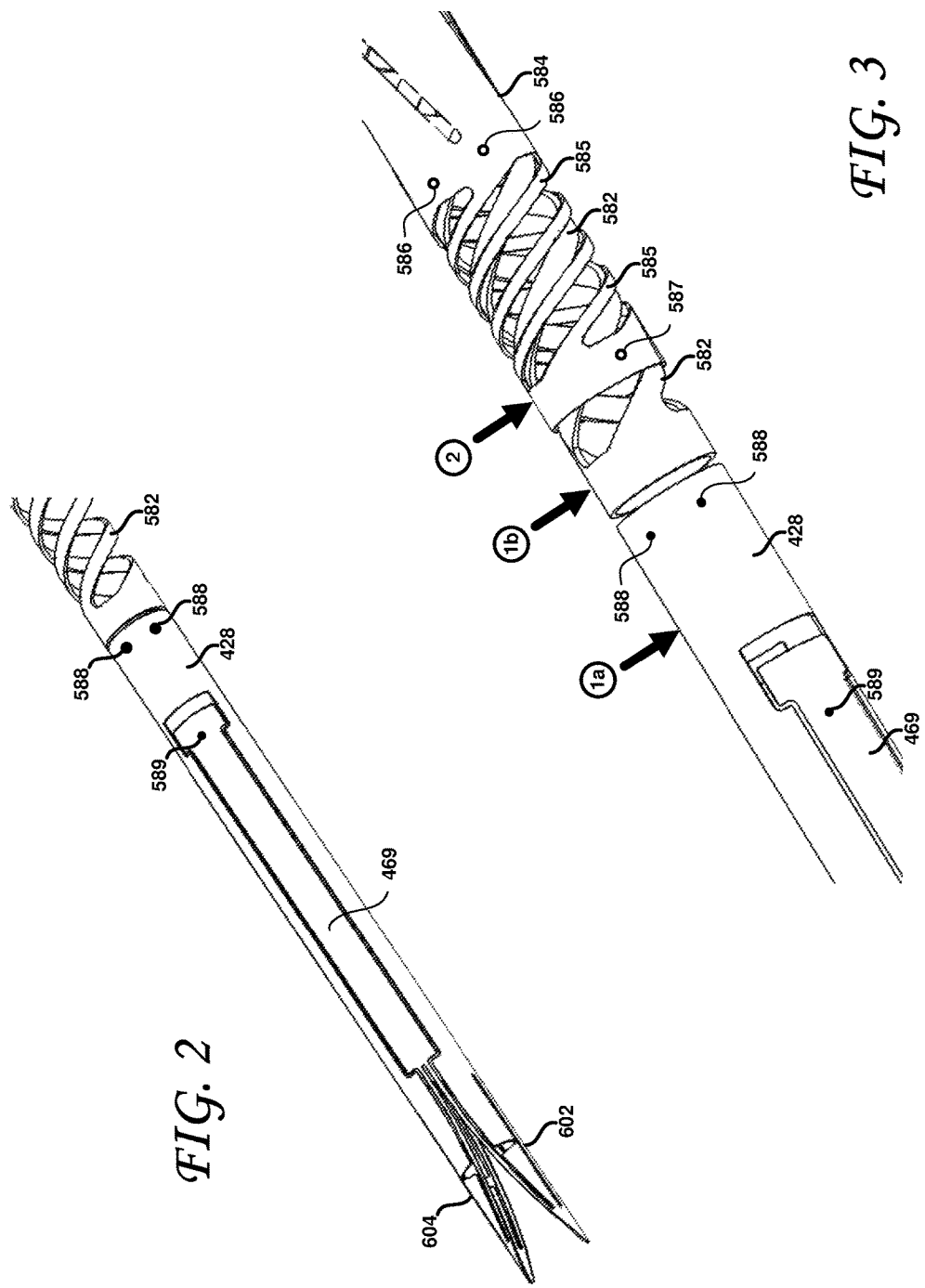

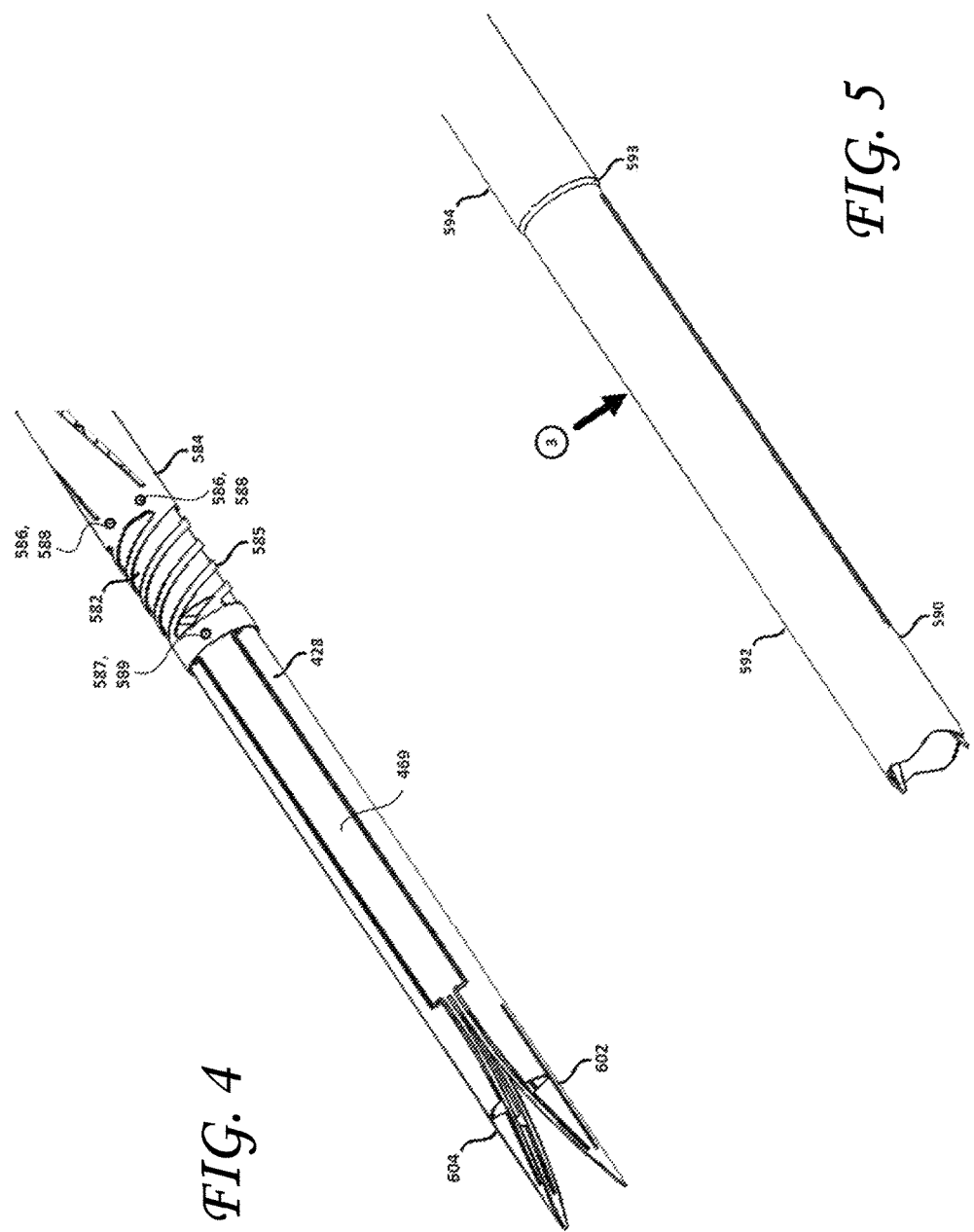

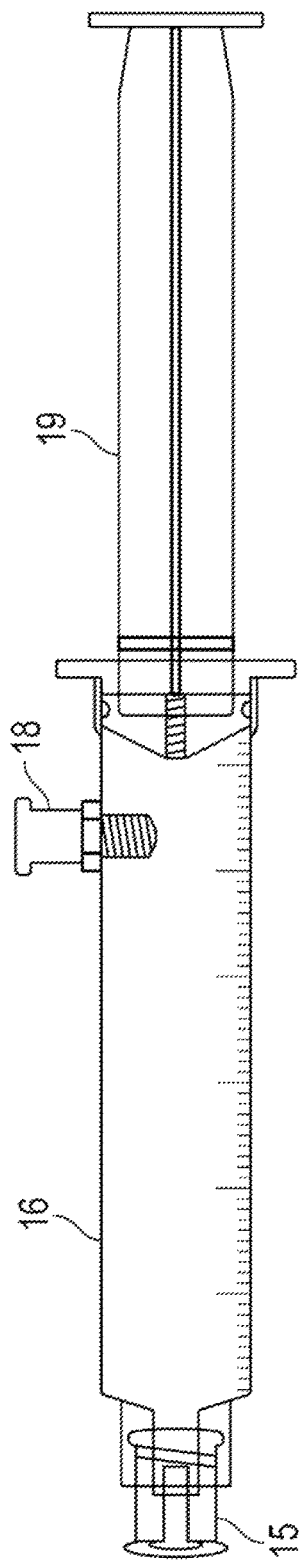
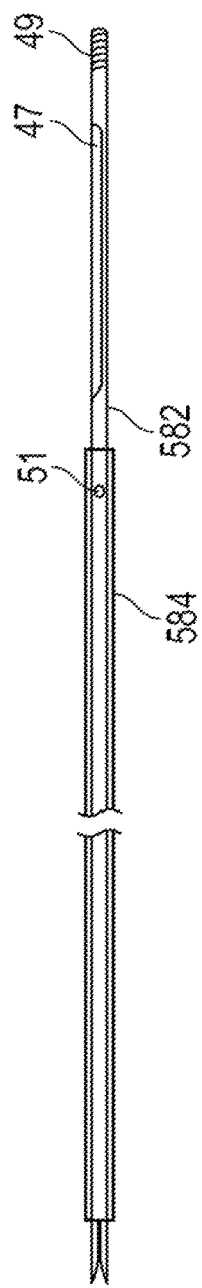
FIG. 6
FIG. 7

DEVICES AND METHODS FOR SOFT TISSUE BIOPSY AND TISSUE SAMPLE COLLECTION

BACKGROUND

Embodiments relate to medical devices and methods. More particularly, embodiments relate to single or multiple insertion, single or multiple sample biopsy medical devices.

SUMMARY

Embodiments are drawn to medical devices and methods that are used for single insertion, single sample and single insertion, multiple sample biopsies, including advanced features for fine needle aspiration. Embodiments may comprise structures and functionality for tissue penetration, coring, capturing, parting off and retrieving soft tissue samples from a target biopsy site for subsequent pathological analysis. Other embodiments may comprise structures and functionality configured for penetration, coring, capturing, parting off and retrieving of tissue and materials other than soft tissue. Embodiments may be portable, disposable or reusable and may be mechanically, manually or electrically powered and operated.

A soft tissue biopsy device may comprise a monolithic work assembly, a tissue collection assembly and a vacuum source. A soft tissue biopsy device, according to one embodiment, may comprise mechanisms that simultaneously provide distal open-end coring blade actuation, blade exposure and internal vacuum to core, transport and store tissue samples of any chosen length. Mechanisms may simultaneously provide distal open-end coring blade actuation, blade exposure and internal vacuum to core, transport and store multiple tissue samples of any chosen length with a single insertion. One embodiment may include structures for simultaneously providing distal open-end coring blade actuation, blade exposure and internal vacuum to core, transport and store tissue samples of any chosen length and, at the end of each cycle, resetting itself to permit closed beak penetration to other sites during a single insertion. A soft tissue biopsy device may comprise, according to embodiments, mechanisms that simultaneously provide distal open-end coring blade actuation, blade exposure and internal vacuum to core, transport and store tissue samples of any chosen length, as well as the ability to extract, transport, separate from solid samples and separately store any amount of liquid from the site of biopsy.

One embodiment is a method comprising open-ended coring, transport and storage of multiple samples of any chosen length of solid and semi-solid tissues during a single insertion. One method comprises open-ended coring, transport and storage of multiple samples of any chosen length of solid and semi-solid tissues as well as extracting, transporting and separately storing any desired amount of liquids from the biopsy site during a single insertion.

A device, according to one embodiment, may use a direct plunger in longitudinal action to actuate coring and part-off, as well as to, with the same motion, and with hard stops, precisely control exposure of beak tips during coring and also precisely control and limits travel for creating the ideal exposure and streamlining during closed-beak penetration. One embodiment of a device may be configured to provide direct and positive tactile feel for both configurations (closed beak penetration/part-off configuration and open beak coring configuration), with beak exposure optimized in the range of >0.000" to 0.030" for coring and beak exposure at or near the flex-point for penetration/part-off. According to one embodiment, a standard syringe may be used for the purpose of longitudinal actuation of the beaks. A standard syringe may also be used to provide a fully sealed, visible vacuum chamber.

According to one embodiment, a standard detent-enabled syringe may be used to hold the positions of closed-beak penetration/part-off and open beak coring configurations. Continuous vacuum may be enabled, according to one embodiment, using a syringe modified with a side-port. According to one embodiment, such a side-port modified syringe may be used such that the side port constitutes a travel limiter to preserve the forward mechanism integrity during firm part-off of tissue. A side-port-modified syringe may be used with a selectable valve attachment to permit continuous, selectable vacuum as well as injection of materials. One embodiment includes a method of modifying a standard syringe plunger to interface with an inner tube or tube sets. A method may be carried out, to modify a standard syringe plunger to create the ability to fine tune distances to set or "zero-out" the ideal distance for holding beaks open even during maximum vacuum, without requiring the operator to manually hold that position during coring, in detent-equipped off-the-shelf syringes.

One embodiment includes a method of enabling a range of part-off pressures in detent-equipped syringes by adding a side-port limiter for forward travel. One method comprises creating a travel-limiting tab on tube sets to set the distance dimensions in an otherwise uncontrolled (operator simply provides forwards/backwards movement "to-the-stops") assembly. A slot may be created to limit tab-travel that not only sets the end points of tab excursion, which incidentally accounts for the additive distances of exposure of beaks plus the amount of travel needed to activate the two configurations, closed and open, but also enables assembly by a two-part slot, one end (the proximal limit or end point) being formed by the syringe distal edge (which is used to set the detent precisely by the syringe manufacturer), and the other edge (the distal edge of the slot) being formed by a u-shaped slot in the over-tube/Luer hub assembly. The overtube assembly may be attached to the syringe after the tube set is torqued onto the plunger with calibration provided by the tube set tab being in contact with the distal syringe edge with the plunger over the detent on the detent's proximal side, with beaks fully open and exposed to the correct range.

One embodiment is a method of sealing the actuation slot formed by the over-tube and syringe distal edge with a sealed dust cover (e.g., shrink wrap or the like) such that the entire system with the exception of the distal tip of the tube set is sealed for vacuum. A standard off-the-shelf syringe may be modified, according to one embodiment, to become a visible, vacuum-sealed storage chamber, that can be easily emptied by unscrewing the suitably modified plunger. A standard off-the-shelf syringe may also be modified and utilized as a sample-visible storage chamber that can be easily emptied after collecting multiple samples (during a single insertion for example) and can be reassembled by re-attaching the syringe plunger to prepare for further sampling One embodiment includes adding a "pinching" foot pedal in the vacuum line (if a continuous vacuum source is used) to control vacuum during a procedure. Any vacuum source may to be added, according to one embodiment, to a side-port-modified syringe for the purposes of fluid evacuation, tissue transport, part-off augmentation, and ultrasound visualization (surge vacuum provided by pinch-off foot pedal for example). A sequential fluid flush and vacuum may

BRIEF DESCRIPTION OF THE DRAWINGS

FIG. 2 is a side perspective view of a monolithic work assembly of a soft tissue biopsy device, according to one embodiment;

FIG. 3 is a side view of unassembled components of a tube set of a soft tissue biopsy device, according to one embodiment;

FIG. 4 is a side view of assembled components of a tube set of a soft tissue biopsy device, according to one embodiment;

FIG. 5 is a side view of a tube set with overtube of a soft tissue biopsy device, according to one embodiment;

FIG. 6 is a side view of a modified hypodermic syringe and associated components of a soft tissue biopsy device, according to one embodiment;

FIG. 7 is a view of an assembled proximal end of a tube set of a soft tissue biopsy device, according to one embodiment;

DETAILED DESCRIPTION

Reference will now be made in detail to the construction and operation of embodiments illustrated in the accompanying drawings. The following description is only exemplary of the embodiments and methods described and shown herein. The embodiments and methods, therefore, are not limited to these implementations, but may be realized by other implementations.

According to one embodiment, a tissue biopsy forward coring and part off device, also referred to herein as an excisional device, may be configured to retrieve multiple samples of normal and/or abnormal appearing biological tissues or other materials during a single insertion through the skin (percutaneous procedure) into the, for example, soft or hard tissue area of the body from which the biopsy is taken. Embodiments may comprise structures and functionality for different phases of a multi-phase biopsy procedure, which may be performed by hand or with sufficient modification by attachment to a stereotactic table stage or Magnetic Resonance Imaging (MRI) stage. Embodiments of a biopsy device, along with associated related subcomponents described herein, may provide the capability to retrieve solid, contiguous and/or fragmented tissues as well as liquid and semi-solid tissues for analysis, diagnosis and treatment. Embodiments described and shown herein are related to co-pending and commonly assigned U.S. patent application Ser. No. 13/973,898 entitled "SOFT TISSUE CORING BIOPSY DEVICES AND METHODS"; U.S. patent application Ser. No. 14/050,771 entitled "SOFT TISSUE CORING BIOSPY DEVICES AND METHODS"; U.S. patent application Ser. No. 62/052,070 entitled "SOFT TISSUE BIOPSY OR EXCISIONAL DEVICES AND METHODS"; U.S. patent application Ser. No. 62/052,591 entitled "IN-SITU MATERIAL DELIVERY DEVICES AND METHODS"; and U.S. patent application Ser. No. 61/876,977 entitled "TISSUE CORING BIOPSY DEVICES AND METHODS", the entire disclosures of which are hereby incorporated herein in their entirety.

Figure 1:
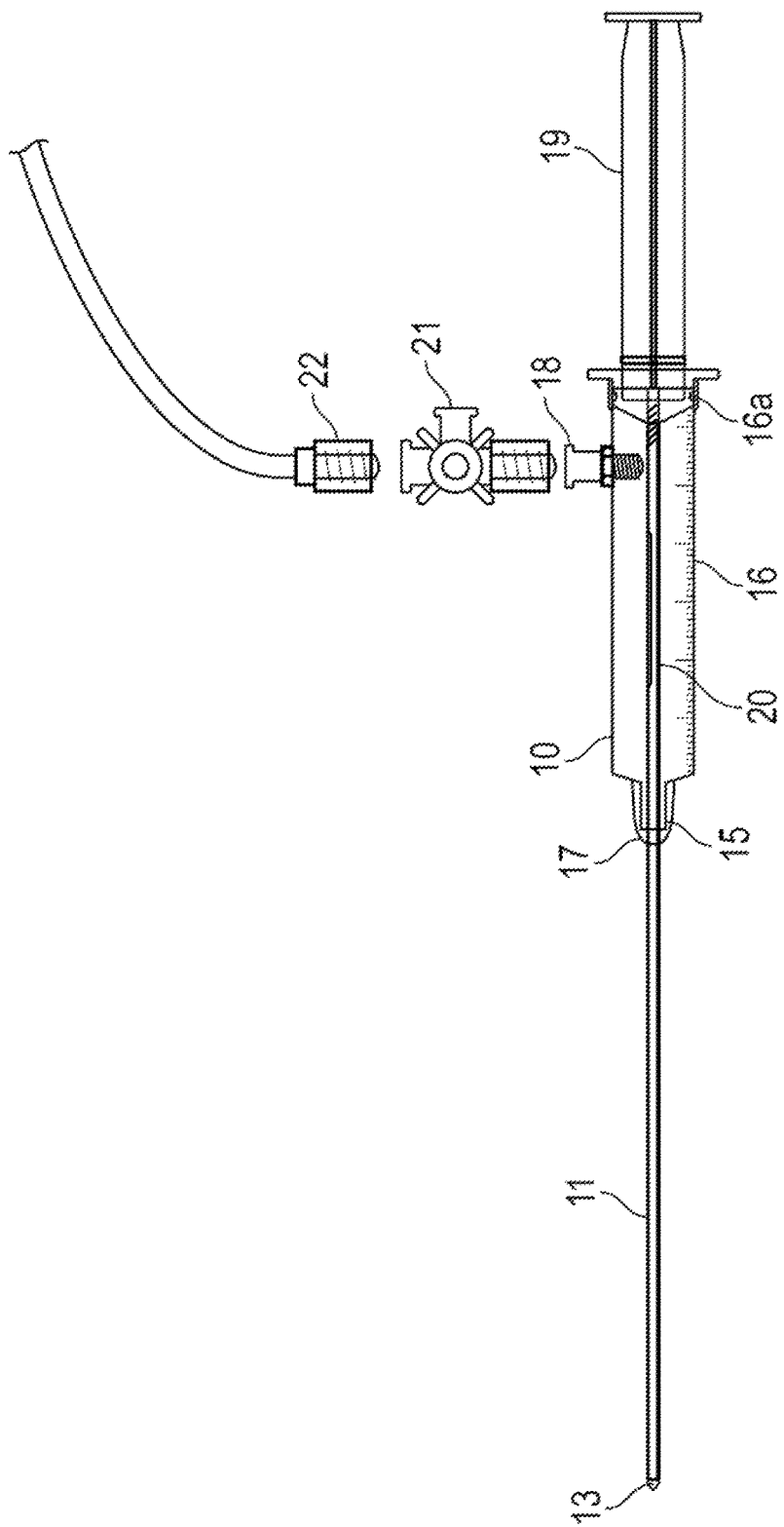
FIG. 1 is a side view of a soft tissue biopsy device, according to one embodiment.

FIG. 1 is a side view of a soft tissue biopsy device 10, according to one embodiment. In this view, a work element 13 comprising a coring beak or beaks is at the distal end of a tube set 11. The tube set 11 is connected through a standard double female Luer lock 15 to a hypodermic syringe 16 with detent 16a. The proximal tube 20 with a longitudinal slot is connected to the stopper of the syringe plunger 19 by a threaded machine screw extension, as shown in this figure. Tapped and threaded into the barrel of the syringe 16 is a standard threaded female Luer lock connection, to which may be attached a standard medical three-way stopcock 21, directly to a standard medical Luer lock tube 22 or simply to an additional syringe (not shown). A further breakdown and disclosure of the various components of device 10 may be found in the following paragraphs, according to embodiments and methods.

FIG. 2 is a side perspective view of a monolithic work assembly of a soft tissue biopsy device, according to one embodiment. In this figure, a monolithic work assembly 428, referred to herein in other figures as work assembly 13, comprising cutting beaks, living hinges and actuation tendons may be seen. The beaks 602 and 604, with their living hinges shown by slots and tendons that extend nearly to the tip of the beaks and are connected to a tendon actuation tab 469 may be formed of a single hypo tube with laser cuts, for example, to allow actuation of the beaks 602 and 604. If the tendon actuation tab 469 is held stationary while the body of the work assembly 428 is pushed distally, and assuming the beak tips to be the distal end of the device 10, then the beaks may be closed by action of the tendons pulling on the beaks 604 and 602, which flex over their incorporated living hinges for either tissue penetration or to part off cored tissue and other materials. Also shown in this view is a proximal extension or proximal tube 582 of the work element, which may also be laser cut from a single hypo tube in a helical pattern for flexibility or left as a solid tube. Also shown in this figure are weld or glue-locating spots 588 and 589, as will be further discussed below.

FIG. 3 is a side view of an unassembled tube set of a soft tissue biopsy device 10, according to one embodiment. In this figure, the portion labelled 1a represents the monolithic beak work assembly 428; 1b refers to the proximal tube extension, shown previously as proximal tube 582 in this figure and the previous figure; and 2 refers to a laser cut distal tube, which covers the proximal tube 582 and the proximal portion of the work assembly 428, shown slid proximally for ease of visualization. The weld spots 588 located on the most proximal end portion of the work assembly 428 and 589, located on the tendon actuation tab 469, correspond to the weld holes 586 and 587 of the distal tube 584. Thus, once aligned, the actuation mechanism shown by the helix structure 585 of the distal tube 584 may be fixed to the work element 428 by welding or gluing the weld holes 586 and 587 to the corresponding weld spots 588 and 589, respectively. In this manner, holding the distal tube 584 stationary at the proximal end of the soft tissue biopsy device 10 while pushing distally the inner or proximal tube 582 will serve to close the beaks, and an opposite action will serve to open them.

FIG. 4 is a side view of assembled elements of a tube set of a soft tissue biopsy device 10, according to one embodiment. In this figure, it may be seen that the distal tube 584 has been slid distally to align its weld holes and spots with the work assembly 428. Relative axial motion between the inner proximal tube 582 and the outer distal tube 584 induced by distally or proximally directed forces acting on at least one of them will cause the work assembly 428 beaks 602 and 604 to open and close, as desired. The combined elements illustrated in this figure may be referred to herein as a tube set, for ease of understanding.

FIG. 5 is a side view of a tube set with overtube 592 of a soft tissue biopsy device 10, according to one embodiment. The portion designated as 3 in this figure indicates an overtube 592 covering the assembled tube set of FIG. 4, and which may be formed from a single stainless steel hypo-tube or other materials, such as polyimide, PET or other materials as a sheath. It may be of one single diameter over its axial length or may have features such as a shoulder 593 and enlarged diameter proximal portion 594. It may also have other features such as slots 590, and may be cut perpendicularly at its distal tip or have other conformational features, such as the sine wave shown in this figure. The distal tip of the overtube 592 may be blunt, tapered or sharpened, according to embodiments.

FIG. 6 is a side view of a modified hypodermic syringe 16 and associated elements of a soft tissue biopsy device 10, according to one embodiment. In this view, a standard hypodermic syringe incorporating a Luer type connection at its distal end and a single detent, shown as elements 16 and 16a in FIG. 1 above, at the proximal end to engage the internal stopper has been drilled and tapped towards the proximal end of the syringe tube barrel to accept a standard Luer type female connection 18, the threaded end of which extends into the barrel of the syringe body. Other methods of attaching this Luer type female connection, such as drilling and gluing, or simply incorporating such a feature into a pre-manufactured custom syringe barrel may be envisioned, and are thus considered to be within the scope of this specification. Attached to this connection may be a standard medical grade three-way stopcock with a male and female connections, also shown as item 21 in FIG. 1, to select pathways for fluids or aspiration as shown above in FIG. 1. Additionally, the rubber stopper and plunger 19 have been drilled and tapped longitudinally to accept a machine screw, as will be discussed further below. Again, a specially manufactured syringe plunger and stopper capable of accepting a machine screw or self-tapping screw may be envisioned, and are thus considered within the scope of this specification. Finally, the modified syringe is attached at its distal end to a standard double female Luer type connector 15, which has itself been modified to include a slot on its proximal or distal end, according to embodiments. Finally, the syringe 16 may be of any standard or custom size or dimension, and may be modified as necessary to bore its distal end to a dimension that allows free axial sliding of the tube set, depending on the outer diameter of the tube set to be used, which may be of any desired dimension, according to embodiments.

FIG. 7 is a view of an assembled proximal end of a tube set of a soft tissue biopsy device 10, according to one embodiment. In this view, and referring to FIGS. 2 through 5 above, the distal tube 584 of the assembled tube set has been cut away some distance, such as 3.5" or other dimension, from the proximal end of the proximal tube 582. The proximal tube 582 has been cut away approximately 1.25" or other dimension to form an elongated slot 47 that may be equivalent in width to the diameter of the tube or other dimension on one side, and the slot has been filled with a proximally upward sloping internal ramp, which may be formed of any of a number of filling materials, such as plastic or glue, or may simply be formed by laser cutting on the distal three sides of the intended slot and pressing the flap thus formed into the inner lumen of the proximal tube 582, according to methods. The proximal end of the proximal tube 582 has been filled with a machine screw 49 with exposed threads, and the machine screw may be placed therein by tapping the end of the proximal tube 582, by laser welding or soldering the machine screw in place, or simply by gluing it in place, according to embodiments. The machine screw, which may also be a self-tapping screw, is of a pitch and diameter to allow it to be mated to the modified plunger 19, passing through the stopper of the modified syringe as discussed under FIG. 6 above. Additionally, the distal tube 584 has been configured with a travel limiting dimple or tab 51 on its outer surface, which may be formed by crimping, laser welding, soldering or gluing, according to embodiments.

Referring now to a combination of the views of FIG. 1, FIG. 6, and FIG. 7, and according to one embodiment, a device 10 may be assembled by sliding a tube set 11 through the double female Luer connector 15 into the body of a modified syringe 16 until the machine screw 49 of the proximal tube 582 engages the threads of the tapped syringe plunger 19 through the rubber stopper, or, in the case of a self-tapping screw, may be introduced into a hole formed in the syringe plunger 19. The tube set may be configured to be free to slide within the distal end of the syringe 16, and the dimple or tab 51 of the distal tube 584 of the tube set may be configured to slide within a distal slot cut into the double female Luer connector 15, with the most proximal travel of the tube set limited by the dimple 51 stopping against the distal end of the hypodermic syringe 16 itself, which by differential axial travel between the distal tube 584 and the proximal tube 582 of the tube set may result in a beak open configuration of the distal work (beak) assembly (indicated as 13 FIG. 1) of the device (labeled as 10 FIG. 1), as shown in FIG. 7. Because of this configuration, the calibration of the beak(s) fully open position may be easily obtained by placing the syringe 16 stopper/plunger 19 in the rearmost detent position and turning the plunger 19 until the beaks are fully open with the dimple 51 resting against the tip of the syringe 16, resulting in a zeroed configuration of the device 10 with the beak(s) open. Forward or distal travel of the plunger/stopper 19 may be limited ultimately by the stopper running against the female Luer connector 18 in the barrel of the syringe 16, as well as by another hard stop mechanism discussed below. If an overtube 594/592, such as that shown if FIG. 5 above, slotted at its proximal end a distance equal to the total travel desired for the dimple 51 to begin to close the beaks of the work (beak) assembly 13 is fitted by gluing to a male Luer connector, the overtube may be slid over the tube set and engaged into the double female slotted Luer connector 15 of FIGS. 1 and 6. Alternatively the overtube 594 may simply be glued or otherwise fastened directly to the female Luer by gluing, or it may be of a single piece with female Luer configuration incorporated into its proximal end, for reversible attachment of the assembly to the syringe 16. The overtube 594 may also be attached to a double female Luer in such a way as to allow overtube 594 to rotate about its longitudinal axis in which case the double female Luer would be constructed with a proximal slot to also form the distal edge of the slot constraining forward travel of the distal tube, according to one embodiment. In either case forward travel of the distal tube 584 will be limited to the dimple 51 reaching the most forward limit of the slot in the overtube 594, or double Luer if such double Luer includes a proximal slot edge, and any remaining travel of the proximal tube 582 will result in fully closing the beaks 13 (as shown above in FIG. 1) at the distal tip of device 10. Any overly zealous pushing on the plunger 19 may be cushioned by the stopper abutting the female Luer connector 18, as discussed above, in order to avoid overdriving the beaks closed for either part off or penetration functions of the device 10. The overtube 594 may be supplied with a vacuum tight sleeve of rubber or other material, such as a sprayed on coating, to cover the slot in which the dimple 51 rides, such as at 17 of FIG. 1 above, according to embodiments. The overtube 594 may serve to allow the beaks of the work element 13 to open under the shelter of the distal end of the overtube, as shown previously in FIG. 5 above, but also to allow the tube set 11 to move an optimal distance distally for coring and parting off phases of a tissue sampling procedure with the beaks extending further out of the distal end of the overtube 594, according to embodiments and methods.

A significant advantage of the device 10 is its simplicity in use. If the plunger 19 is pressed forward over the detent in the syringe 16, the beaks will be remain in closed position as held there by the distal edge of the syringe detent, for ease of single handed manipulation of the device during tissue penetration to a target site. The detent enables an operator to concentrate on delicate advancement through the tissues on the way to the target, without needing to be concerned about keeping the beaks closed with additional manual forward pressure on the plunger. Once the target site has been reached, the plunger 19 may be pulled back proximally over the detent, such as detent 16a in FIG. 1 above, to the detent proximal edge, which will hold it in that position without further operator effort even while vacuum may be applied through a three-way stopcock valve 21 attached to the female Luer connector 18 or by other means. In this position, the beaks of the work element 13 are fully open and coring may begin with a rotational movement or twisting movement of the device 10, according to methods, without requiring the operator to hold retraction forces on the plunger to keep the beaks open. This automatic holding position greatly simplifies the procedure enabling an operator to concentrate on delicately advancing the needle (tube set assembly) through the target area in order to core a sample. It also enables a portable, optional driver (not shown), which may be motor or spring driven for example, to be utilized to twist the entire syringe/tube set assembly with no further mechanism needed to maintain the beaks in coring position. A coring position of the beaks may be defined as widely open or of any desired open configuration, exposed an optimal distance from the distal edge of the overtube, according to methods. As each sample that is cored is then parted off as a result of the plunger 19 being pushed forward to its most distal position to close the beaks, the samples will be transported proximally into the barrel of the syringe 16, which functions in this configuration as both an actuation mechanism to open and close the beaks of the work element 13, as discussed above, but also serves as a collected tissue storage magazine/vacuum chamber, with vacuum being supplied through the female Luer connector 18 from an externally connected source, such as a second ordinary syringe, portable vacuum pump, or wall suction in a hospital or clinical setting (not shown), according to embodiments. Repeating the procedures described above may result in multiple tissue samples being gathered in a single percutaneous insertion, according to methods. Further, if a three-way stopcock 21 is fitted to the female Luer connector 18 of the modified syringe 16, vacuum suction and delivery of fluids to the target site may be alternately applied by positioning the valve of the stopcock 21 as appropriate for such methods. Fluids thus introduced to a biopsy site may be partially re-aspirated and the irrigation fluid/aspirate collected in a receptacle fitted to the vacuum source for later cytological analysis to enhance diagnostic capabilities provided by the core tissue or material samples, according to methods.

Figure 8:
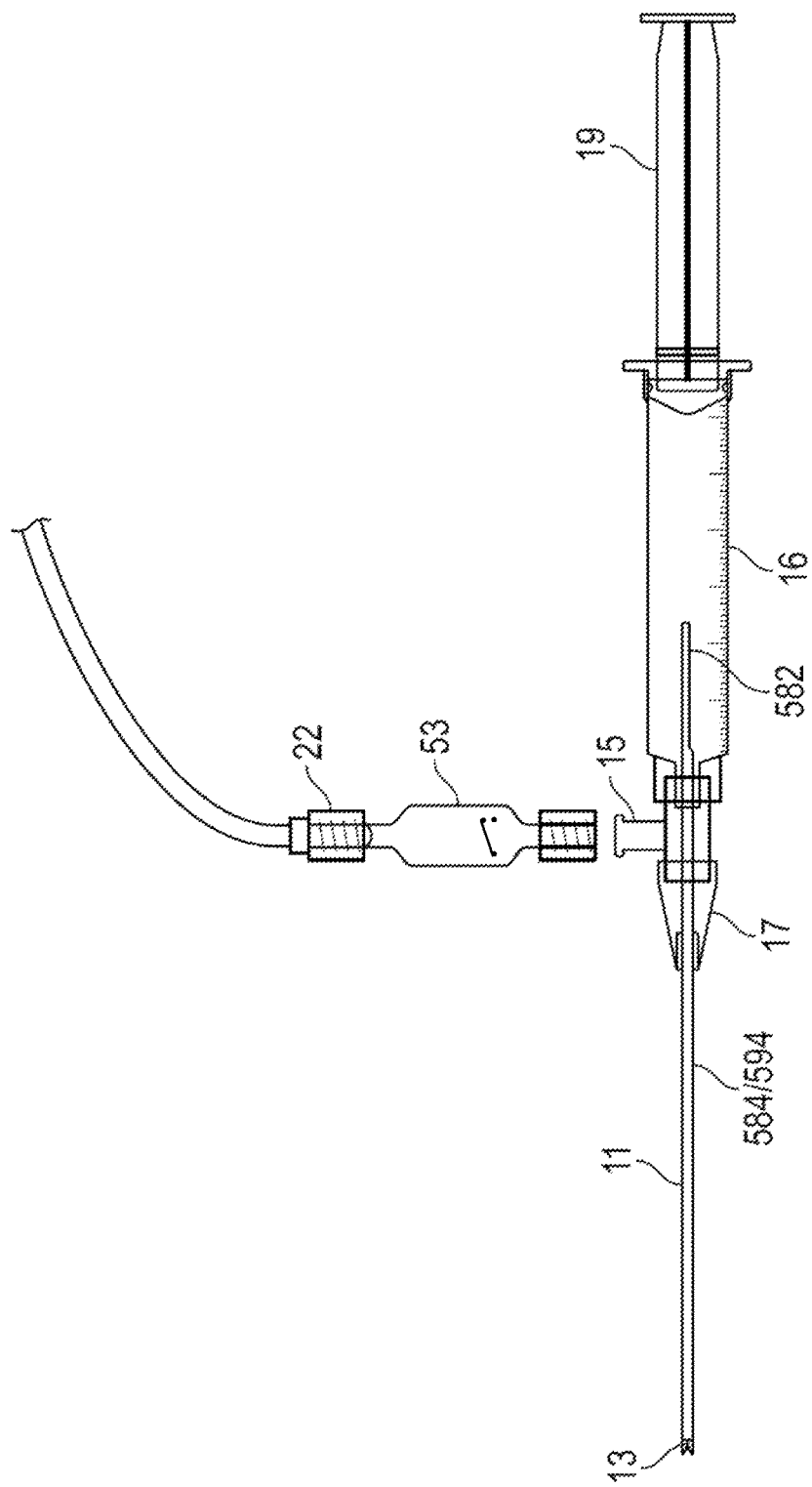
FIG. 8 is a side view of another embodiment of a soft tissue biopsy device, according to embodiments.

FIG. 8 is a side view of another embodiment of a soft tissue biopsy device 10, according to one embodiment. In this view, a standard unmodified hypodermic syringe 16 is connected to a three-way standard medical grade Luer connector 15, and attached to the "T" connection port is a standard Luer one-way valve 53 and tubing 22, which allows air or fluids from the barrel of the syringe 16 to be discharged, according to methods. The tube set 11 with its work element beak(s) 13, as similarly described in FIGS. 1 and 2 above, and consisting of a proximal tube 582 and distal tube 584 similar to those of FIGS. 3 and 4 above, and an overtube 594 of similar to that of FIG. 5 above is connected to a male Luer connector 17, such that the proximal tube 582 is free to slide through the Luer connectors into the body of the syringe 16, while the distal tube and overtube may be fixed into the male Luer connector 17 by gluing their proximal ends or by other means, according to embodiments. The proximal tube 582 is slotted at its proximal end to allow any collected tissue samples to drop into the barrel of the syringe 16 as they are obtained. If the plunger and stopper 19 of the syringe are pushed forward to push the proximal tube 582 distally, the beak(s) of work element 13 will close for tissue penetration or parting off procedures. If the plunger and stopper 19 of the syringe 16 are pulled to the rear, the beak(s) of work element 13 will open and vacuum may be applied to the central lumen of the tube set, allowing coring and transport functions to occur. Once a specimen has been cored, pressing the plunger/stopper 19 forward will expel any air or fluids collected towards the one way Luer valve and tubing without expelling any tissue samples collected in the tube set to be expelled back into a target sample site, and if pressed until the stopper engages the proximal tube 582, will close the beak(s) of the work element 13 and part off the cored sample. In such manner, tissue may be cored and parted off sequentially, and even if the samples are not fully transported to the barrel of the syringe 16, they will be stacked sequentially inside the tube set until enough samples have been obtained to fill the tube set, as desired for a specific operation. If the samples are transported by vacuum to the barrel of the syringe, the syringe may be intraoperatively switched for a second syringe by disconnection at the Luer connector 15. The Luer one-way valve and tubing may be connected externally to a vacuum source and/or collection bottle, according to embodiments. Tissue samples that are not collected in a syringe or syringes 16 may be removed from the tube set 11 at the end of a procedure with the use of a plunger or ramrod (not shown) passing through the tube set from either end, according to methods. If the steps outlined above are followed sequentially, multiple samples may be gained with a single percutaneous insertion to a target tissue site. An advantage of this simplified embodiment is that it incorporates standard medical grade components, such as standard unmodified syringes, Luer connections and valves, and collection vacuum systems and bottles in conjunction with a tube set 11 constructed as described for this figure. Assembly of such an embodiment simply involves attaching the various components via standard Luer connections.

Figure 9:
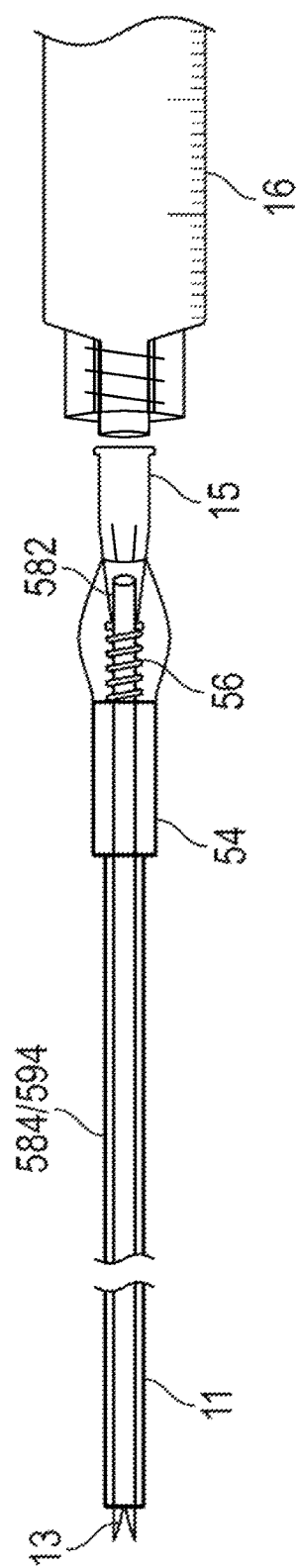
FIG. 9 is a side view of another embodiment of a soft tissue biopsy device, according to embodiments.

FIG. 9 is a side view of another embodiment of a soft tissue biopsy device 10, according to embodiments. In this figure, another mechanism is described wherein the tube set 11 described in the previous figure, including overtube 594, distal tube 584 and proximal tube 582 are all connected to a single female Luer connector 15. In this embodiment, the proximal tube 582 is glued to the female Luer connector 15, leaving the proximally shortened distal tube and overtube free to slide longitudinally to actuate the beak(s) of the work element 13 independently of an attached syringe 16. The distal tube 584 and overtube 594 are held by a sleeve 547 which is attached to a flexible seal over a spring 56 to the proximal tube 582 at its connection with the Luer connector 15. The spring acts between the sleeve holding the distal tube/overtube and the Luer connection to which is fixed the proximal tube 582, and may be of sufficient tension to maintain the beak(s) of the work element 13 open during forward coring. Beak actuation is therefore manually operated by sliding the combined distal tube and overtube glued or fixed into their sleeve longitudinally, and pulling the sleeve proximally will close the beaks and allowing the sleeve with its spring to relax distally will open the beaks of the work element 13. A butterfly actuator (not shown) may contain the spring 56, be fitted to sleeve 54 and female Luer 15 such that squeezing the butterfly actuator may in class 1, 2 or 3 lever arm configuration provide leverage and action effects to slide the sleeve in the desired direction (proximally and distally with respect to syringe 16) and an easily releasable locking tab may be included to keep sleeve 54 desirably positioned during part-off or penetration operations, to permit easier one handed manipulations, according to embodiments. In another embodiment, sleeve 54 may be constructed of two parts that slide over each other, allowing connection of overtube 594 to one portion and distal tube 584 to another portion of sleeve 54, thus allowing for additional optional differential axial movement between the two outermost tubes of a tube set 11.

Collection of tissue samples with procedures similar to those described above, but with the exception that the beaks of work element 13 may be operated independently of vacuum supplied by the attached syringe 16, may be accomplished, according to methods. It should also be understood that combinations using selected components of these embodiments would be within the scope of all of them, enabling instrument 10 to be tailored to specific clinical needs and applications, according to various embodiments.

Figure 10A:
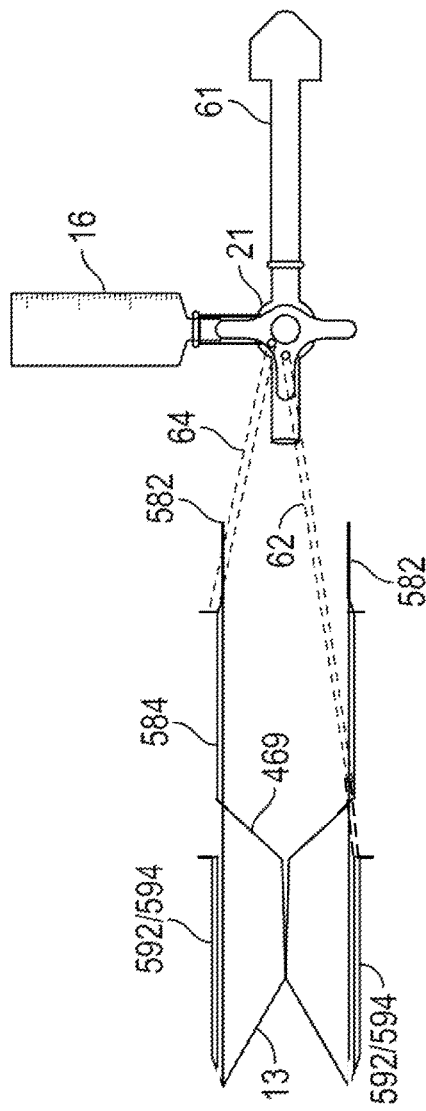
FIGS. 10a, 10b and 10c are side views of another embodiment of a soft tissue biopsy device, according to embodiments.
Figure 10B:
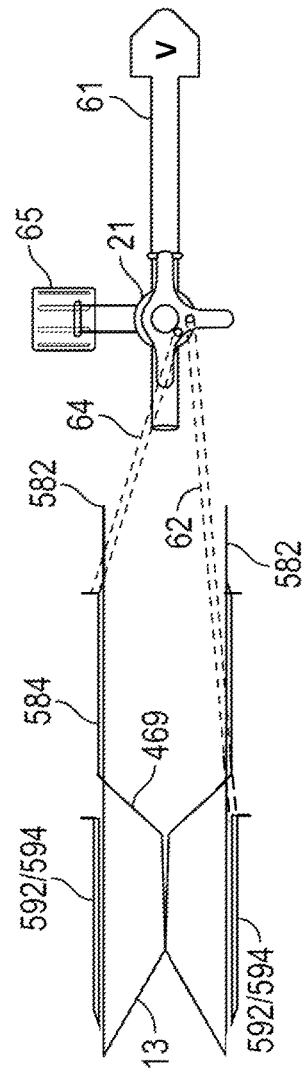
Figure 10C:
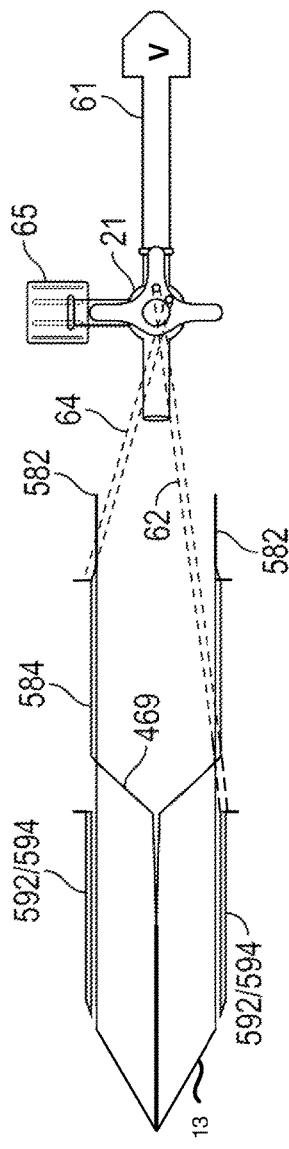

FIGS. 10a, 10b and 10c are side views of another embodiment of a soft tissue biopsy device 10 in different phases of use, according to embodiments and methods. In these figures, another mechanism is described wherein the tube set 11 described in the previous figure, including overtube 594, distal tube 584 and proximal tube 582 are all included as in FIG. 9; however in this embodiment, only proximal tube 582 is fitted with a Luer or friction-fit, tapered fitting to which a modified three-handle stopcock 21 is fitted. Since only proximal tube 582 is fixed to the stopcock in a non-moving way, both distal tube 584 and overtube 594/592 are able to move under the control of the stopcock 21 through connecting rods 64 and 62 respectively.

The three illustrations in FIGS. 10a, 10b and 10c represent three states of use of biopsy device 10, according to one embodiment. In FIG. 10a, the device is in a configuration for an injection step via syringe 13e 16. In this view, a vacuum source indicated by 61 may be attached and as may also be true for embodiments illustrated in FIGS. 8 and 9, this vacuum source may be a syringe, a vacuum pump or other source of vacuum, such as vacuum that may be stored in a canister for example. In FIG. 10a, during injection, vacuum would not be needed as indicated by the absence of the letter "V". In FIG. 10b, a cap 65 replaces syringe 16 when no longer needed. In this view, stopcock 21 is rotated to coring position, where connecting rod 64 moves only slightly with respect to its distance from its distal attachment point to distal tube 584. This slight movement causes beaks 13 to open even tighter against overtube 594 in preparation for coring and receiving a maximum-size core tissue sample. Simultaneously the same stopcock 21, due to its rotation to coring position, moves overtube 594 proximally far enough to expose beak 13 cutting edges to the tissue being cored. At the same time, a vacuum source 61 that is connected is now activated as indicated by the letter "V", which will act to enhance coring and receiving tissue into biopsy device 10. Once the desired coring is completed, it can be seen that in FIG. 10c the stopcock 21 is further rotated to its part-off/penetration position which retracts the overtube 594 even further for optimum streamlining (penetration configuration) of the distal end of device 10 including its beaks 13 and overtube 594 and also acts to further retract distal tube 584, which by means of its connection to the beak assembly 13 via the tendon tab 469, causes the beaks 13 to tightly close parting off the core sample from its host tissue. In the FIG. 10c, the vacuum source is still connected and vacuum is still being applied as indicated by the letter "V" in vacuum source 61, while stopcock 21 is suitably constructed to continue to permit flow in the desired direction, including tube set 11 to vacuum forces.

As noted for these figures, the position of the stopcock 21 and corresponding positioning of overtube 594 and distal tube 584 in this configuration is well suited for penetration since the beaks are closed and the overtube is drawn proximal to reside in a retracted position streamlining the cross-section profile of tube set 11 of the biopsy device 10. In such configuration vacuum forces need not be applied during penetration operations. In such an embodiment, as in those shown in FIGS. 8 and 9, standard connections and vacuum sources may easily be connected, interchanged and controlled, (for example with a foot-pedal) as desired.

In this embodiment, overtube 594 is attached via connecting rod 62 such that distance is precisely controlled however overtube 594 may be allowed to rotate with respect to the rest of biopsy device 10 including with respect to tube set 11. Given that connecting rod 62 may be attached to overtube 594 by a bushing or other suitable sliding connection, overtube 594 is free to rotate and may also be held still or rotated differentially from tube set 11 such that surrounding tissue may be spared from rotational forces of the outer surfaces along the length of tubular components of biopsy device 10. In this embodiment tube set 11 may be manually rotated or may be placed in an auxiliary rotational power unit and rotated by any other suitable rotational mechanism such as electrical, spring or air power for example.

Figure 11:
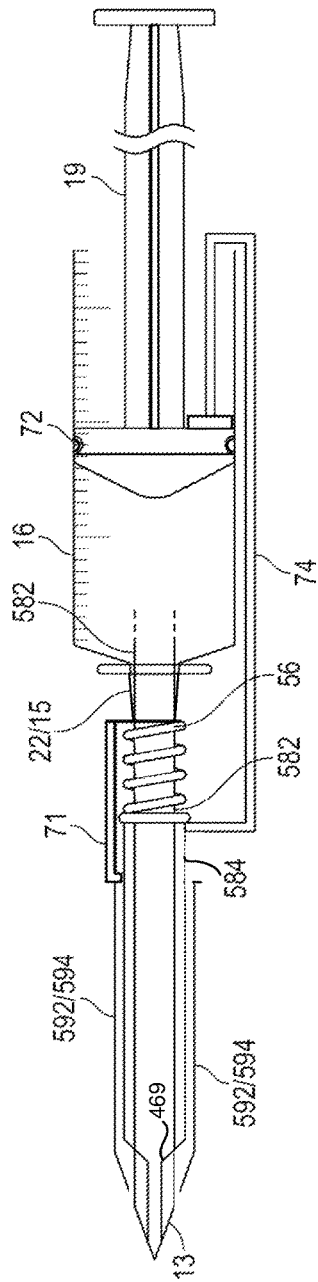
FIG. 11 is a side view of another embodiment of a soft tissue biopsy device, according to embodiments.

FIG. 11 is a side view of another embodiment of a soft tissue biopsy device 10, according to embodiments. In this figure, another mechanism is described wherein tube set 11 described in the previous figure, including overtube 594, distal tube 584 and proximal tube 582 are all included as in FIGS. 10a, 10b and 10c and similar to those figures, in this embodiment only proximal tube 582 is fitted with a Luer or friction-fit, tapered fitting 22/15, to which a standard syringe 16 may be fitted. In this illustration, syringe 16's barrel is fitted with an incorporated detent as indicated at 74, which holds the plunger/stopper assembly 19 in place once plunger/stopper 19 is placed in position over the detent as shown.

In this illustration, overtube 592/594 is fixed by strut 71, however it is to be understood that this strut may be movable if desired to retract overtube 594 to a more optimal position. Distal tube 584 is connected to beak assembly 13 via tendon tab 469 (tab 469 and its attachment to beak assembly 13 is previously shown in detail in FIG. 2) and is held in forward position by spring member 56, unless and until strut 74 is acted upon by plunger/stopper assembly 19 at the detent position within standard syringe 16. At this position, syringe 16 may still be applying vacuum forces to the central lumen of tube set 11, however a slight proximal movement of actuating strut 74 may now cause beak assembly 13 to close for parting off of the cored sample.

When plunger/stopper assembly 19 is advanced forward to make contact with the proximal end of proximal tube 582, beaks 13 may also close such that biopsy device 10's distal end will be in a streamlined position with beaks closed for penetration without the need for application of vacuum and since overtube 594 and distal tube 584 are at the forward limit of their travel, the beaks may emerge distally to a streamlined position and also in a closed configuration for penetration. As in the embodiment described in FIGS. 10*a*, 10*b* and 10*c* above, the embodiment illustrated in FIG. 11 may be constructed in such a way that overtube 592/594 may be rotated differentially with respect to tube set 11 and therefore may also be held in non-rotation while tube set 11 may be rotated either manually or by any other suitable powered rotation mechanism.

According to methods, an operator may use a device 10 of the various embodiments described herein that can simultaneously provide vacuum to aid coring, part-off and transport of tissue specimens throughout these cycles with a straight-through tube that is fully open from distal working end to proximal deposition end that terminates in a collection chamber to which vacuum is applied during a tissue or material collection procedure. Such a device may provide controlled exposure of working coring beaks in a range of exposure that is proportional to diameter of the tube holding the working beaks. Such a device may be configured of a tubular coring and part-off device whose coring and part-off functions are actuated with a straight push-pull mechanism that does not extend outwards or inwards in order to fully open and fully close the work element 13 beak(s). Such a device may provide beak tip exposure such that the majority of the cutting edge of the beaks is substantially parallel to the direction of rotation or oscillation of the beaks. Such a device may have a differentially rotating outer tube that provides a sharpened distal end that enables maximum streamlining of the distal end of the device during closed-beak tissue penetration. Such a device may provide rotational friction minimization during closed beak penetration. Such a device may provide a differentially rotating outer tube that protects the beak mechanism by covering all but the most distal cutting edge of the beaks ranging from zero exposure to approximately 0.060" exposure among tubular diameters of approximately 0.020" to 1" or more. Such a device may provide automatic exposure-holding of beak exposure by controlling overtube axial position. Such a device may include provisions for automatic wide open position holding of working coring beaks. Such a device may provide an automatic beaks closed position for parting off of tissue and other materials. Such a device may provide automatic beaks closed exposure control to maximize streamlining of the distal tube area by controlling the position of an overtube in relation to other portions of such a device.

According to other methods and various embodiments described herein, such a device 10 may be manually oscillated or rotated with one hand while all other functions including vacuum control, beaks positioning and exposure control and valve positions are separately controllable. Such devices may include a chamber suitable for viewing tissue specimens in real time as they emerge from the proximal end of the coring tube, where the device has an axially aligned wide-open mouth at its distal end and a full diameter pathway to a wide-open proximal deposition end terminating in said collection chamber. Such a tissue-coring device may include the capability of rotating or oscillating it with an additional separate auxiliary power unit, and may further include the capability of being rotated and oscillated by an auxiliary rotating and oscillating unit while maintaining the outer tube as a non-rotating or differentially rotating member of the device. A tissue-coring device 10 may include a valve that enables alternating injection and vacuum during various stages of a procedure including between coring cycles. A tissue coring device may include a mechanism to simultaneously open the working beaks while changing the exposure of such beaks such that they may open under the protection of an overtube and emerge widely open from under the protection of the overtube for coring. A tissue-coring device as described herein may include a mechanism to simultaneously cause the working beaks to close fully to part-off tissue while changing the exposure of the beaks by retracting the overtube to an area approximating the largest diameter of the living hinge backbone of said beaks, such that streamlining for movement through tissue is maximized. A tissue coring device 10 may, simultaneous with beak closing, rotate the working tubes to enable shearing action of the beaks as they close. A tissue-coring device 10 may provide asymmetric cycle times automatically using a mechanism such as a barrel cam to simultaneously control beak opening and closing along with beak exposure using differential movement of an overtube 594 as described herein. Such a tissue-coring device may provide asymmetric cycle times automatically using a mechanism such as a barrel cam to simultaneously control beak opening and closing along with beak exposure using differential movement of an overtube, while also providing vacuum throughout the coring, part-off and transport cycles. Such a tissue-coring device may provide asymmetric cycle times automatically using a mechanism such as a barrel cam to simultaneously control beak opening and closing along with beak exposure using differential movement of an overtube, while also providing vacuum throughout the coring, part-off and transport cycles, while also being capable of semi-automatic and/or fully automatic cycling.

According to still further embodiments and methods, a method of carrying out a coring, parting off and sample tissue transporting cycle or cycles under conditions of continuous vacuum may be advantageous as the various phases of coring, parting off and transport of a sample may be carried out under the added force of vacuum to aid in the performance of each of these functions. According to methods, a device 10 may be advantageously used to provide infinitely and continuously selectable tissue sample length, equating to a real time selection function during a procedure as is possible only with open-ended devices at both distal and proximal ends since an open ended configuration of the tube sets such as described herein for device 10 permits continuous forward movement of the sampling tube sets, bringing more target tissue into the distal end of the tube sets and without constraining the core sample once it reaches the proximal deposition point.

According to another method, a tissue sampling method using a device 10 may be agnostic to the consistency of the tissues and fluids being sampled. Such procedures as draining lesions, transudate, exudate, relieving pressure, coagulation, active bleeding, soft and firm tissues may all be easily sampled without bias introduced by the need to bend or force tissue into a trough as is the case for all side cutting devices and is also the case for any open-mouth type devices that do not include continuous vacuum and where any fluids are captured and automatically separated from tissue samples. A tissue and fluid sampling device 10 as described herein may automatically capture and separate fluids and solid tissues while continuing to sequentially operate through the phases of penetration and coring, with continuing vacuuming and sample transport. A method may also include drawing a target lesion towards and into the forward open end of a biopsy and fluid sampling device 10, with advantages such as real time, selective vacuum moving of a lesion, such as a hemorrhagic papilloma combined with a precision approach, gentle sampling, and a precise feel factor that are inherent in the various embodiments of a device 10.

It is to be understood that the above descriptions are but exemplary methodologies using various embodiments of device 10, and that one or more of the elements or steps described above may be omitted, while other elements or steps may be added thereto, and further that different embodiments of device 10 may be used in methods described herein, depending on the requirements of the target tissue to be sampled from any site within the body. Other operator method embodiments and device embodiments are supported as well. The order of some of the steps described herein may additionally be changed, according to a desired procedure.

It is also to be understood that any dimensions referred to herein are exemplary in nature only. Those of skill in this art will recognize that other dimensions and/or configurations may be implemented, depending upon the application, and that the elements of the device could be of any length or dimension, all of which are considered within the scope of this disclosure. Furthermore, any discussion of dimensions or ranges of dimensions or physical or dynamic aspects such as flow rates or ranges of motion or time factors outlined herein are exemplary in nature only and should not be considered to be limiting.

The entire device may be configured to be disposable or may be configured to be reusable in whole or in part. Embodiments of the present device may be modified to be electrically powered by one or more motors and batteries and/or external power sources through an electrical coupling to connect to an external power supply conveniently placed, for example, in the handle or proximal end of the present biopsy device. The entire device may also be internally or externally manually powered, mechanically powered or be powered by means such as compressed air, gas or pressurized fluid. The present device may be formed of or comprise one or more biocompatible materials such as, for example, stainless steel or other biocompatible alloys, and may be made of, comprise or be coated with polymers, such as polyimide, and/or biopolymer materials as needed to optimize function(s). Some of the components may be purposely surface-treated differentially with respect to adjacent components, as detailed. If used, any of the various gears or pulleys may be made of any suitable, commercially available materials such as nylons, polymers such as moldable plastics, and others. If used, a motor powering the various powered functions of the present biopsy device may be a commercially available electric DC motor. The handle of the present device may likewise be made of or comprise inexpensive, injection-molded plastic or other suitable rigid, easily hand held strong and light-weight material. The handle may be configured in such a way as to make it easily adaptable to one of any number of existing guiding platforms, such as stereotactic table stages. The materials used in the present biopsy device may also be carefully selected from a ferro-magnetic standpoint, such that the present biopsy device maintains compatibility with MRI equipment. Any power source used may comprise an external commercially available AC to DC transformer approved for medical device use and plugged into the provided socket in the present biopsy device, or may comprise an enclosed battery of any suitable and commercially available power source. The battery may be of the one-time use disposable (and optionally recyclable) variety, or may be of the rechargeable variety. Additionally, other power sources, for example, mechanical linkages or compressed air motors, may be used.

While certain embodiments of the disclosure have been described, these embodiments have been presented by way of example only, and are not intended to limit the scope of the disclosure. Indeed, the novel methods, devices and systems described herein may be embodied in a variety of other forms and other applications. All such other applications making use of the principles disclosed herein for this device and that could be envisioned by one skilled in the art are therefore considered to be within the scope of this disclosure. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures and dimensions thereof may differ from those shown in the figures. Depending on the embodiment, certain steps described in the example above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A device, comprising:
 a syringe comprising a body portion and a plunger portion configured to engage with and slide axially within the body portion;
 a tube set fitted to the syringe, the tube set comprising:
 a proximal tube attached to the plunger portion at a proximal end thereof and terminated, at a distal end thereof, by a beak assembly such that a radius of curvature of an inner surface of all of the proximal tube and of an inner surface of all of the beak assembly is unchanged from a proximal end of the proximal tube to a distal tip of the beak assembly, the beak assembly being configured to assume a first open configuration suitable for coring through tissue and a second closed configuration suitable for tissue penetration and parting off tissue; and a distal tube disposed over and coupled to the proximal tube to enable travel-limited axial displacement relative to the proximal tube;

wherein axially moving the plunger portion within the body portion of the syringe causes differential axial movement of the proximal tube relative to the distal tube to cause the beak assembly to selectively assume the first open or the second closed configuration.

2. The device of claim 1, further comprising a first structure within the body portion of the syringe and a second structure on the distal tube, wherein the first structure is configured to engage with the second structure to limit the axial displacement of the distal tube relative to the proximal tube.

3. The device of claim 1, further comprising a connector assembly fitted to the body portion, the connector assembly enabling a vacuum to be drawn within the body portion of the syringe.

4. The device of claim 3, wherein the connector assembly comprises a selectable valve enabling at least aspiration and fluid evacuation from the body portion of the syringe.

5. The device of claim 1, further comprising an overtube disposed over the tube set, a proximal end of the overtube being secured to a distal end of the body portion of the syringe and a distal end of the overtube partially covering the beak assembly.

6. The device of claim 1, further comprising a spring configured to keep the beak assembly in the first configuration while coring through tissue.

7. The device of claim 1, wherein the proximal tube and the beak assembly are cut from a single tube of material.

8. The device of claim 1, wherein the beak assembly comprises a first and a second beak, each comprising a first and second tendon separated by a living hinge, wherein the differential axial movement of the proximal tube relative to the distal tube selectively pushes and pulls on the first and second tendons to selectively cause the beak assembly to assume the first or the second configuration, respectively.

9. The device of claim 1, wherein the body portion of the syringe is further configured to contain tissue cut by the beak assembly.

10. The device of claim 1, configured to cut a first tissue sample having a first length and a second tissue sample of a second, different length and to store the first and second tissue samples in the body portion.

11. The device of claim 1, wherein the proximal tube comprises an elongated slot disposed therein, the elongated slot being configured to enable cut tissue to be drawn from a lumen of the proximal tube to the body portion.

12. A method, comprising:
providing a syringe comprising a body portion and a plunger portion configured to engage with and slide axially within the body portion;
fitting a tube set to the syringe, the tube set comprising:
a proximal tube attached to the plunger portion at a proximal end thereof and terminated, at a distal end thereof, by a beak assembly such that a radius of curvature of an inner surface of all of the proximal tube and of an inner surface of all of the beak assembly is unchanged from a proximal end of the proximal tube to a distal tip of the beak assembly, the beak assembly being configured to assume a first open configuration suitable for coring through tissue and a second closed configuration suitable for tissue penetration and parting off tissue; and a distal tube disposed over and coupled to the proximal tube to enable travel-limited axial displacement relative to the proximal tube; and axially moving the plunger portion within the body portion in a first direction to cause differential axial movement of the proximal tube relative to the distal tube and to cause the beak assembly to assume the first open configuration;

advancing the beak assembly within tissue and collecting cored tissue within the proximal tube; and axially moving the plunger portion within the body portion in a second direction to cause differential axial movement of the proximal tube relative to the distal tube and to cause the beak assembly to assume the second closed configuration that cuts and separates the cored tissue from surrounding tissue and collecting the parted-off cored tissue within the proximal tube.

13. The method of claim 12, further comprising causing a first structure within the body portion and a second structure on the distal tube to engage with one another to limit the axial displacement of the distal tube relative to the proximal tube when the plunger portion is moved.

14. The method of claim 12, further comprising drawing a vacuum through a connector assembly fitted to the body portion.

15. The method of claim 14, further comprising selecting to aspirate or evacuate fluid through a selectable valve fitted to the body portion.

16. The method of claim 12, further comprising fitting an overtube over the tube set, a proximal end of the overtube being secured to a distal end of the body portion and a distal end of the overtube partially covering the beak assembly.

17. The method of claim 12, further comprising keeping the beak assembly in a coring configuration for a time using a spring.

18. The method of claim 12, wherein fitting comprises cutting the proximal tube and the beak assembly from a single tube of material.

19. The method of claim 12, wherein fitting comprises configuring the beak assembly with a first and a second beak, each comprising a first and second tendon separated by a living hinge, and wherein axially moving the proximal tube relative to the distal tube selectively pushes and pulls on the first and second tendons to selectively cause the beak assembly to assume the first or the second configuration, respectively.

20. The method of claim 12, further comprising storing tissue cut by the beak assembly in the body portion.

21. The method of claim 12, wherein axially moving comprises cutting a first tissue sample having a first length and cutting a second tissue sample of a second, different length and storing the first and second tissue samples in the body portion.

22. The method of claim 12, wherein axially moving is carried out manually by an operator's hand moving the plunger portion relative to the body portion.

* * * * *